United States Patent
Schreiner et al.

(10) Patent No.: US 10,800,357 B2
(45) Date of Patent: Oct. 13, 2020

(54) DYNAMIC DISINFECTION METHOD FOR A VEHICLE DRINKING WATER TANK

(71) Applicant: Airbus Operations GmbH, Hamburg (DE)

(72) Inventors: Axel Schreiner, Bremen (DE); Paolo Cavarero, Hamburg (DE)

(73) Assignee: Airbus Operations GmbH (DE)

( * ) Notice: Subject to any disclaimer, the term of this patent is extended or adjusted under 35 U.S.C. 154(b) by 71 days.

(21) Appl. No.: 15/973,940

(22) Filed: May 8, 2018

(65) Prior Publication Data

US 2018/0257584 A1 Sep. 13, 2018

Related U.S. Application Data

(60) Division of application No. 14/077,457, filed on Nov. 12, 2013, now abandoned, which is a continuation of
(Continued)

(30) Foreign Application Priority Data

May 13, 2011 (DE) .......................... 10 2011 101 471

(51) Int. Cl.
*B60R 15/00* (2006.01)
*B64D 11/02* (2006.01)
(Continued)

(52) U.S. Cl.
CPC .............. *B60R 15/00* (2013.01); *A61L 2/18* (2013.01); *B60N 3/18* (2013.01); *B64D 11/02* (2013.01);
(Continued)

(58) Field of Classification Search
CPC ....................................................... B67D 1/07
See application file for complete search history.

(56) References Cited

U.S. PATENT DOCUMENTS 3,719,191 A 3/1973 Zimmerly
6,770,150 B1 * 8/2004 Duckett .................... A61L 2/18
134/10
(Continued)

FOREIGN PATENT DOCUMENTS

CN 1633246 A 6/2005
DE 199 58 290 A1 6/2000
(Continued)

OTHER PUBLICATIONS

Chinese Office Action dated Feb. 25, 2015 (Page 7 categorizing cited references).

*Primary Examiner* — Matthew D Krcha
(74) *Attorney, Agent, or Firm* — Lerner, David, Littenberg, Krumholz & Mentlik, LLP

(57) ABSTRACT

A method for disinfecting a vehicle drinking water tank is designed for dynamic disinfection. By providing a vehicle drinking water tank with a spray diffuser, which is arranged inside the vehicle drinking water tank, the disinfecting liquid can be sprayed over substantially the entire inner surface of the tank. Partial filling of the drinking water tank with a disinfecting liquid starts the disinfection method. The dynamics of the disinfection method are achieved by spraying the disinfecting liquid in such a way that a moved film of disinfecting liquid is formed and wets an inner surface of the drinking water tank. Material transport at the inner wall of the tank is improved and mechanical shear forces act on the biofilm, which is to be removed and/or disinfected, in combination with the biochemical disinfection forces.

5 Claims, 3 Drawing Sheets

Related U.S. Application Data application No. PCT/EP2012/058791, filed on May 11, 2012.

(60) Provisional application No. 61/485,776, filed on May 13, 2011.

(51) Int. Cl.

| | |
|---|---|
| *C02F 1/68* | (2006.01) |
| *C02F 1/50* | (2006.01) |
| *A61L 2/18* | (2006.01) |
| *B60N 3/18* | (2006.01) |
| *B64D 11/04* | (2006.01) |

(52) U.S. Cl.
CPC .................. *C02F 1/50* (2013.01); *C02F 1/68* (2013.01); *B64D 11/04* (2013.01); *C02F 2201/008* (2013.01); *C02F 2209/02* (2013.01); *C02F 2303/04* (2013.01)

(56) References Cited

U.S. PATENT DOCUMENTS

| | | | |
|---|---|---|---|
| 6,861,033 B2 | 3/2005 | Mullins et al. | |
| 2001/0002656 A1 | 6/2001 | Schnegg et al. | |
| 2004/0007255 A1* | 1/2004 | Labib | ........................ A61L 2/18 134/30 |
| 2005/0121057 A1 | 6/2005 | Knowlton et al. | |
| 2005/0126927 A1 | 6/2005 | Lindauer et al. | |
| 2006/0193760 A1 | 8/2006 | Hight | |
| 2008/0017586 A1 | 1/2008 | Matousek et al. | |
| 2009/0152183 A1 | 6/2009 | Stewart et al. | |

FOREIGN PATENT DOCUMENTS

| | | | | |
|---|---|---|---|---|
| DE | 200 13 686 U1 | 12/2000 | | |
| DE | 20013686 U1 * | 12/2000 | ............... | B67D 1/07 |
| DE | 103 49 158 A1 | 6/2005 | | |
| DE | 10 2004 030 859 A1 | 1/2006 | | |
| DE | 603 06 525 T2 | 2/2007 | | |
| DE | 10 2009 009938 A1 | 8/2010 | | |
| GB | 2 407 585 A | 5/2005 | | |
| WO | 03/070024 A1 | 8/2003 | | |
| WO | WO-03070024 A1 * | 8/2003 | ........... | A23L 3/0155 |

* cited by examiner

DYNAMIC DISINFECTION METHOD FOR A VEHICLE DRINKING WATER TANK

CROSS-REFERENCE TO RELATED APPLICATIONS

The present application is a divisional of U.S. patent application Ser. No. 14/077,457, filed on Nov. 12, 2018, which is a continuation of International Application No. PCT/EP2012/058791, filed May 11, 2012, which claims priority from German Patent Application No. 10 2011 101 471.7 filed May 13, 2011 and claims the benefit of the filing date of U.S. Provisional Patent Application No. 61/485,776 filed May 13, 2011, the disclosures of which are hereby incorporated herein by reference.

FIELD OF THE INVENTION

The invention relates to the disinfection of a drinking water tank. In particular, the invention relates to a vehicle drinking water tank, an aircraft comprising a drinking water tank, and a dynamic disinfection method for a vehicle drinking water tank.

TECHNICAL BACKGROUND

In known methods, a static disinfection process is used for mobile water tanks. A disinfecting liquid is fed into the containers and lines to be disinfected so that the entire water system is filled completely with disinfecting liquid. The disinfecting liquid remains in the system for a specific period of time so as to achieve the desired sanitary result. Due to different standards, demands are placed on the reaction time, which leads to long maintenance intervals of the vehicles which contain the drinking water tank. These known disinfection methods can only be carried out if the vehicle is stopped for a sufficiently long period, which complicates fleet scheduling within the scope of fleet management. Furthermore, long periods of downtime mean that high economical costs are incurred for the vehicle operator. Since the disinfection methods already known require the drinking water system to be filled completely, these methods also have a considerable effect on the environment in addition to high costs for the disinfecting active ingredient.

BRIEF SUMMARY OF THE INVENTION

An aspect of the invention provides for improved or accelerated disinfection of a vehicle drinking water tank.

A vehicle drinking water tank, an aircraft comprising a drinking water tank, and a dynamic disinfection method for a vehicle drinking water tank are disclosed.

The embodiments described relate equally to the vehicle drinking water tank, the aircraft, and the method. In other words, features which are described hereinafter with reference to the vehicle drinking water tank are also implemented in the aircraft and are considered to be features of the method, and vice versa.

In accordance with an exemplary embodiment of the invention, a vehicle drinking water tank to be filled with drinking water is disclosed, wherein the vehicle drinking water tank comprises, internally, a surface or an inside surface and wherein the vehicle drinking water tank comprises, internally, a spray diffuser or an inside spray diffuser for wetting and/or moistening and/or sprinkling the surface inside the vehicle drinking water tank with a liquid.

It may thus be possible, by means of the spray diffuser, to provide continuous wetting of the inner surface, which is to be disinfected, of the vehicle drinking water tank by means of a moving liquid film. The disinfecting liquid can be fed into the vehicle drinking water tank through the spray diffuser. For example, this may take place at normal operating pressure in the feed line to the vehicle drinking water tank and at normal operating pressure in the tank. Other pressures are also possible, however. By means of the vehicle drinking water tank according to an embodiment of the invention, it is not necessary to fill the entire tank with disinfecting liquid during the disinfection method. In other words, the vehicle drinking water tank according to an embodiment of the invention enables dynamic disinfection of the contaminated surfaces of the tank, but without having to fill the tank completely with disinfecting liquid. Accelerated disinfection of a vehicle drinking water tank can thus be enabled.

By means of the spray diffuser placed inside the tank, the effective disinfecting active ingredient, which is dissolved in the disinfecting liquid, can be applied directly to the contaminated surfaces. Due to the turbulent falling film of disinfecting liquid produced by the spray diffuser, increased material transport of the disinfecting active ingredient at the inner surface of the tank, which is covered by a biofilm, can be achieved. Improved removal of reaction products and of biological and microbiological material can also be achieved.

In other words, the inner spray diffuser may be arranged in the vehicle drinking water tank in such a way that, due to the discharge of the liquid via the spray diffuser, the disinfecting liquid is distributed over the inner surfaces of the tank in such a way that a hydrodynamically turbulent falling film is created. Due to the force of gravity, the disinfecting liquid flows along the inner surface of the tank and advantageously generates shear forces between the liquid and the contaminated surfaces. Thus, also hydrodynamic turbulences are created and have a mechanical effect on the biofilm and on the contaminated surfaces of the tank and therefore facilitate thorough mixing and/or separation of this biofilm from the inner wall of the tank. In other words, the disclosed tanks and methods utilize a combination both of chemical and biochemical, hydrodynamic action and of mechanical action.

Due to the dynamic spraying of the inner surfaces of the vehicle drinking water tank and the production of a closed circuit with a continuous flow of disinfecting liquid, the amount of necessary disinfecting active ingredient and also the total volume of the disinfecting solution may be reduced on the one hand. On the other hand, due to the increase in concentration of the disinfecting active ingredient at the tank walls as a result of the spraying process and due to the mechanical actions of the falling film, the reaction time may be shortened, which saves valuable time. The advantageous increase in concentration can be deduced from FIG. 5 for example. Time savings during disinfection of a vehicle drinking water tank and also cost reductions for the vehicle operator can thus be achieved.

In other words, by means a closed circuit a vehicle drinking water system with which a continuous flow can be produced during the disinfection method is provided. In other words, the disinfecting liquid circulates in the closed circuit and disinfects all line parts and the tank continuously.

In this and in all other embodiments, the term "disinfection" may be understood to mean the reduction of germs and/or bacteria below a specific threshold value so as to prevent health risks to the users of the water. The entire drinking water system, including lines, can be disinfected more quickly and with less disinfecting liquid and/or disinfecting active ingredient by means of the vehicle drinking water tank according to an embodiment of the invention, since a dynamic disinfection method is thus enabled. By continuously pumping the reduced amount of disinfecting liquid through the lines connected to the tank, said lines are also disinfected in a dynamic manner.

The term "tank" will also be used hereinafter synonymously with the term "vehicle drinking water tank". "Vehicle" can also be understood to mean a watercraft, landcraft, aircraft or spacecraft in this and in any other embodiment. For example, an aircraft can be intended thereby.

In accordance with a further exemplary embodiment of the invention, the spray diffuser is arranged in the vehicle drinking water tank in such a way that the liquid can be distributed in the vehicle drinking water tank in such a way that substantially the entire surface inside the vehicle drinking water tank can be provided with a liquid film, without the vehicle drinking water tank having to be filled completely.

A reduced amount of disinfecting liquid and/or disinfecting active ingredient may thus be sufficient to reach the threshold values for disinfection of drinking water tanks. This can be deduced by way of example from FIG. 5 in terms of the advantageous increase in concentration of the disinfecting active ingredient at the walls of the tank.

In accordance with a further exemplary embodiment of the invention, a vehicle drinking water tank is disclosed in which the spray diffuser is arranged in a central position within a ceiling of the vehicle drinking water tank. For example, this advantageous feature can be deduced from FIG. 1 below. The spray diffuser thus enables a uniform distribution of the disinfecting liquid in all spatial directions inside the water tank. Uniform wetting of the inner surface can thus be ensured. Since the spray diffuser is arranged on the ceiling, the force of gravity can be utilised to produce a dynamic falling film over the inner surfaces of the tank.

In accordance with a further exemplary embodiment of the invention, the vehicle drinking water tank comprises a connected line system, wherein it also comprises a pump device. The line system forms a closed circuit together with the vehicle drinking water tank and the pump device. The connected line system may also be provided spaced apart from the vehicle drinking water tank as a separate part of the aircraft.

By producing this closed circuit, the pump device allows the disinfecting liquid to be pumped continuously, firstly into the tank, where the disinfecting liquid is distributed by means of the spray diffuser according to the invention. Once the formed falling film of disinfecting liquid has disinfected the inner surfaces, the disinfecting liquid runs to the base of the vehicle drinking water tank, where it is collected in lines and pumped further into the line system. A dynamic flow is thus created in the entire vehicle drinking water system, whereby less total liquid has to be used for the disinfection operation due to the active shear forces and the metering of the actual disinfecting active ingredient can also be kept low. This is promoted further by the production of a non-laminar flow and by the desired production of hydrodynamic turbulences in the disinfecting liquid in the tank and in the lines. Such a closed system can be deduced from FIG. 1 for example. In other words, the disclosed tanks and methods utilize a combination both of chemical and biochemical action and of mechanical/hydrodynamic action. A non-laminar flow is thus produced which improves material transport and increases mechanical forces on the biofilm.

In accordance with a further exemplary embodiment of the invention, the vehicle drinking water tank comprises a control unit for controlling the pump device. The control unit is designed in such a way that, in a disinfection mode, it controls the pump device for pumping liquid through the closed circuit in such a way that a continuously moved liquid film is created over the inner surface of the vehicle drinking water tank to be disinfected as a result of continuous liquid discharge via the spray diffuser. The control unit may also be provided spaced apart from the vehicle drinking water tank as a separate part of the aircraft.

In accordance with a further exemplary embodiment of the invention, the vehicle drinking water tank comprises a heating device for increasing or stabilising the temperature of the disinfecting solution.

In other words, the temperature of the disinfecting solution or the disinfecting liquid which is then sprayed inside the tank by means of the spray diffuser and forms a falling film can be increased by means of the disclosed heating device. The disinfection rate thus increases at the same time and an optimal process temperature of the disinfecting solution can be set. Furthermore, it is thus possible to disinfect the vehicle drinking water tank sufficiently quickly in very cold outside areas. For example, by means of the heating device, a drinking water tank of an aircraft can be disinfected sufficiently quickly, even with very cold outside temperatures.

In accordance with a further exemplary embodiment of the invention, the heating device is arranged inside the pump device. The heating device may also be provided spaced apart from the vehicle drinking water tank as a separate part of the aircraft.

In accordance with a further exemplary embodiment of the invention, the pump device is arranged outside the vehicle drinking water tank in a line portion of the line system. The pump device may also be provided paced apart from the vehicle drinking water tank as a separate part of the aircraft.

In accordance with a further exemplary embodiment of the invention, an aircraft comprising a drinking water tank according to one of the exemplary embodiments disclosed above or below is disclosed.

The advantages of disclosed embodiments are particularly noticeable in the specific case of an aircraft drinking water tank, since idle times or ground times of aircraft lead to enormous costs at the expense of the aircraft operator. Due to the shortened reaction times, which can be achieved by means of the tank according to an embodiment of the invention, for carrying out a disinfection operation, valuable time for the operator is saved and the aircraft is operational again more quickly.

According to another exemplary embodiment of the invention, an aircraft comprising a drinking water tank to be filled with drinking water and for generating or facilitating a closed circuit of continuously flowing disinfecting liquid is presented. Therein, the vehicle drinking water tank comprises, internally, a surface and wherein the vehicle drinking water tank comprises, internally, a spray diffuser for wetting the surface inside the vehicle drinking water tank with a disinfecting liquid. Further, the aircraft comprises a connected line system and pump device. Further, the line system forms a closed circuit together with the vehicle drinking water tank and the pump device. Furthermore, the vehicle drinking water tank comprises a control unit for controlling the pump device, and wherein the control unit is configured in such a way that, in a disinfection mode, it controls the pump device to pump disinfecting liquid through the closed circuit in such a way that a moved liquid film is created over the surface of the vehicle drinking water tank to be disinfected as a result of disinfecting liquid discharge via the spray diffuser.

The presented aircraft may be seen as an aircraft with a system for generating or facilitating a closed circuit of continuously flowing disinfecting liquid in the tank and the closed circuit, wherein the system comprises the drinking water tank, the connected line system, the control unit and the pump device mentioned in the previous section. In particular, an aspect of the present invention provides for a disinfecting system for the drinking water tank of an aircraft, which system is configured to carry out the dynamical disinfection method described herein. An embodiment of such a system may be gathered from e.g. FIG. 1.

In accordance with a further exemplary embodiment of the invention, a dynamic method for disinfecting a vehicle drinking water tank is disclosed and comprises the step of providing a vehicle drinking water tank with a spray diffuser inside the vehicle drinking water tank. As a further step, the method comprises the partial filling of the drinking water tank with a disinfecting liquid and comprises the step of spraying the disinfecting liquid, wherein the spraying process is carried out in such a way that a moved film of the disinfecting liquid is formed and wets the inner surface of the drinking water tank. The spraying process can be carried out continuously or quasi continuously for example, whereby a continuously moved film can be produced. Another type of spraying is also possible, however.

In other words, a dynamic, permanently moved flow of disinfecting liquid is produced by the method. This results in the advantages described above and below. The partial filling is thus already initiated by the spray diffuser, but the filling process can also be implemented by other liquid feed lines. Furthermore, the provision of a drain for the proportion of disinfecting liquid which is flowed along the inner walls of the tank can also be included in the method.

A moved liquid film, which is also referred to synonymously as a falling film, is created over the inner walls of the tank by the spray valve. If desired, a continuously moved liquid film can be produced. Due to this spraying of the disinfecting liquid according to aspect of the invention, the tank does not have to be filled completely with liquid. The method according to an aspect of the invention thus wets substantially the entire inner surface of the tank. Since, on the whole, less disinfecting liquid and also less disinfecting active ingredient have to be used, money is saved and the effect on the environment can also be reduced. The vehicle drinking water tank can thus also be disinfected more quickly, which represents valuable time for the aircraft operator for example who applies such a method to an aircraft drinking water tank. The method can be carried out in such a way that at least 20% of the vehicle drinking water tank is filled with disinfecting liquid. This can be prevented if air is sucked into the lines of the system over the course of the method.

In accordance with a further exemplary embodiment, the line system comprises a separate line branch for the delivery of drinking water to a consumer. The separate line branch is connected to the line system in such a way that, in a closed circuit, the disinfecting liquid can also be pumped in the line branch by means of the pump device.

In other words, this embodiment enables a quicker, more cost effective and more environmentally compatible disinfection method in all parts of the vehicle drinking water system, which consists of the tank and the remaining part of the closed circuit.

In accordance with a further exemplary aspect of the invention, the method further comprises the step of providing a closed circuit between the drinking water tank and an outer line system, and further comprises the connection of a pump device, whereby the disinfecting liquid is pumped through the closed circuit.

The advantage of a quicker, more cost effective and more environmentally compatible disinfection operation can thus be utilised advantageously in the entire drinking water system. Areas which are located in separate line branches and which are designed for the supply or delivery of drinking water to a consumer can also be disinfected.

In accordance with a further exemplary aspect of the invention, the method comprises the step of connecting a heating device, whereby the temperature of the disinfecting liquid is changed or kept at a desired value.

In accordance with a further exemplary aspect of the invention, the method comprises the step of measuring the temperature of the disinfecting liquid in the form of a temperature value and the subsequent transmission of the measured temperature value to a control unit. Furthermore, the step of controlling the heating device by means of the control unit on the basis of the measured temperature value is also included in this embodiment.

In accordance with a further exemplary aspect of the invention, the method comprises the checking of a minimal reaction time and the disconnection of the pump device in the event that the minimal reaction time is reached, or the continuance of pump operation in the event that the minimal reaction time is not reached, whereby the vehicle drinking water tank is relieved of the disinfecting liquid. Further steps include the closing of the outlet system and the filling of the vehicle drinking water tank with clean water.

Preferred embodiments of the invention will be described hereinafter with reference to the figures.

BRIEF DESCRIPTION OF THE DRAWINGS

The illustrations in the figures are schematic and are not to scale. In the description of the figures, like reference numerals are used for like or similar elements.

DETAILED DESCRIPTION

Figure 1:
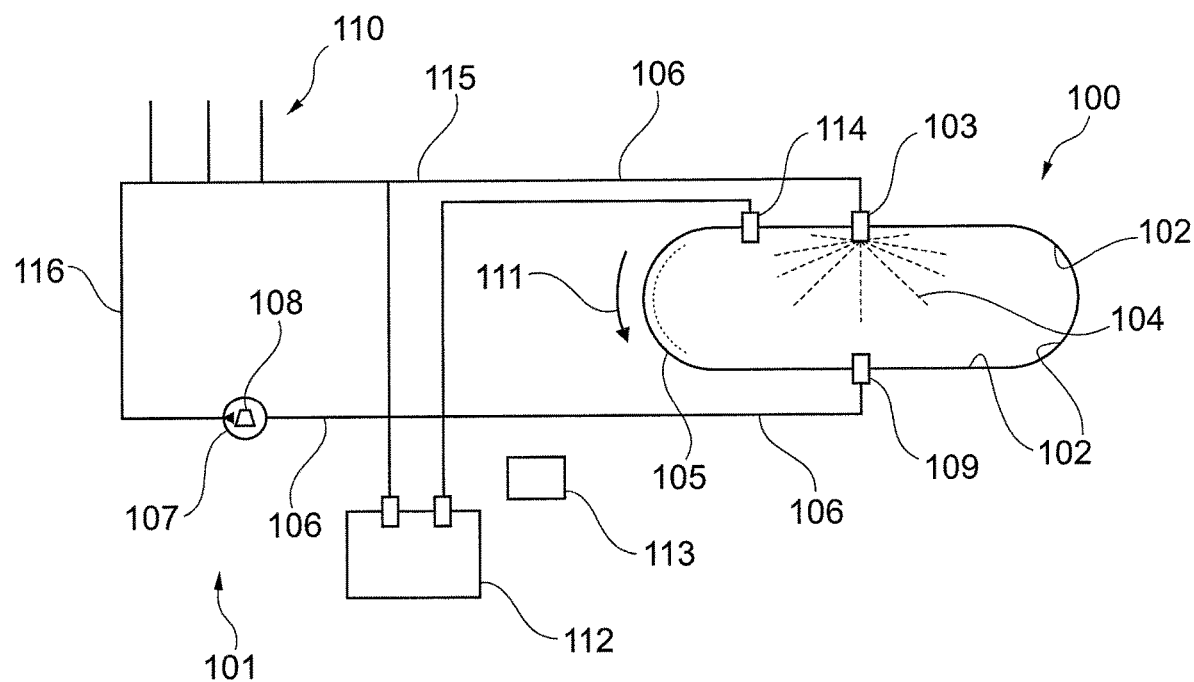
FIG. 1 shows a schematic, two-dimensional illustration of a vehicle drinking water tank according to an exemplary embodiment of the invention.

FIG. 1 shows a vehicle drinking water tank 100 to be filled with drinking water. The vehicle drinking water tank comprises, internally, a surface 102 and further comprises, internally, a spray diffuser 103 for wetting the surface inside the vehicle drinking water tank with a disinfecting liquid 104. As can be seen in FIG. 1, the spray diffuser 103 is arranged centrally in the ceiling of the vehicle drinking water tank. The disinfecting liquid can thus be distributed homogeneously in all spatial directions within the tank, if desired, so that substantially the entire surface inside the vehicle drinking water tank is provided with a liquid film 105, without the vehicle drinking water tank having to be filled completely with disinfecting liquid. The spray diffuser 103 may possibly also be designed as a moved diffuser, for example as a rotary diffuser, so as to wet the surface inside the tank. The arrow 111 indicates that a falling film of disinfecting liquid is concerned, which flows along the inner wall. A dynamic disinfection process is thus possible, as will be described hereinafter. Hydraulic turbulences which improve material transport away from the tank wall so said wall can thus be disinfected more quickly, more cost effectively and with less disinfecting active ingredient are created along the inner walls of the tank as a result of the flow of disinfecting liquid. Shear forces also created during this process and acting on the biofilm at the inner wall of the tank assist the disinfection process by movement, thorough mixing and partial detachment of the biofilm. In other words, the disclosed tanks and methods utilize a combination both of chemical and biochemical action and of hydrodynamic and mechanical action.

Furthermore, FIG. 1 shows the pump device 107 which is located in the connected line system 106. The line system and the vehicle drinking water tank as well as the pump device form a closed circuit 101 so that a small amount of disinfecting liquid can be pumped continuously through the drinking water tank. The heating device 108 is also shown and is located inside the pump device in this case by way of example. The vehicle drinking water tank also comprises an outlet opening 109 in the base of the tank. A separate line branch 110 for delivery of drinking water to a consumer is also shown. In this area too, quick and advantageous disinfection can be achieved by means of the tank according to an embodiment the invention and by means of the method according to an aspect of the invention.

A control unit 112 is also shown and can control an overflow valve 114 for example. The control unit 112 is also able to control and/or adjust the filling and draining of liquid in the tank. Numeral 116 denotes a water feed line, whereas 115 denotes a return line. Furthermore, a control unit 113 is provided which is designed in such a way that it coordinates the interaction between the components shown. Improved disinfection can be achieved throughout the entire illustrated closed circuit by means of the tank and/or by means of the dynamic method. As can be seen from FIG. 1 the control unit 112, the pump device 107 and the heating device 108 may also be provided spaced apart from the drinking water tank 100 as a separate part or feature.

Figure 2:
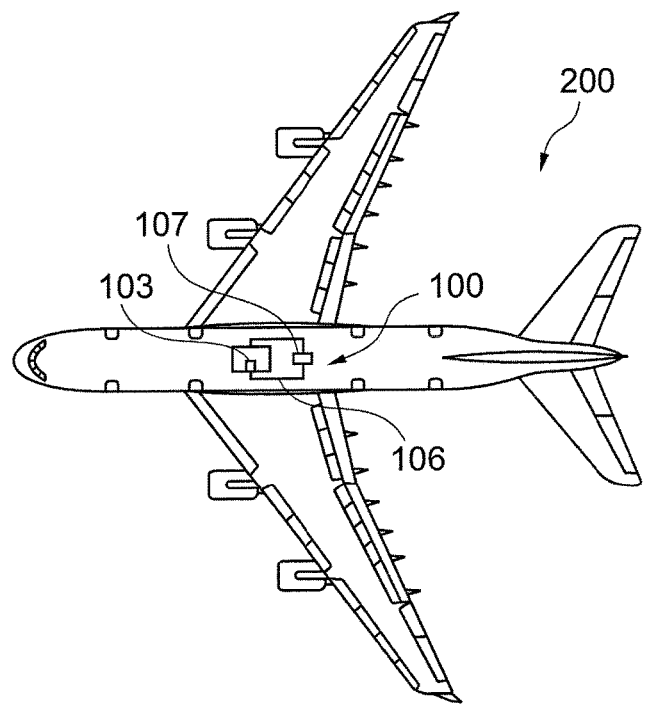
FIG. 2 shows a schematic, two-dimensional illustration of an aircraft comprising a drinking water tank according to an exemplary embodiment of the invention.

FIG. 2 shows an aircraft 200 comprising a drinking water tank 100 according to an exemplary embodiment of the invention. The tank, which comprises a spray diffuser 103 and a pump device 107, allows a dynamic disinfection method by means of the spray diffuser. Furthermore, a connected line system 106 is contained, whereby, on the whole, a closed circuit is formed which can also be disinfected.

Figure 3:
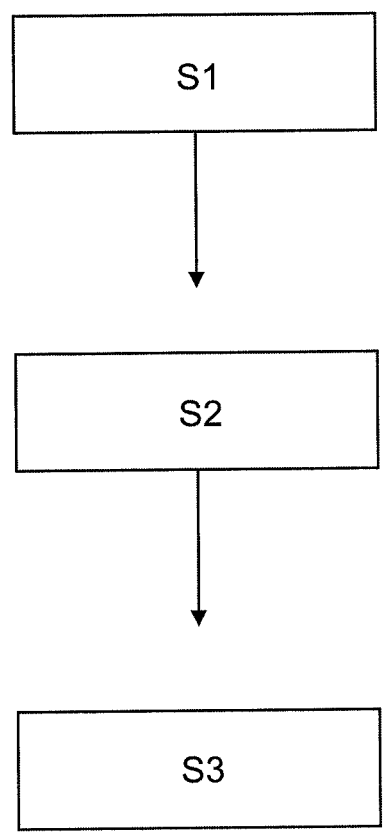
FIGS. 3 and 4 show flow diagrams of dynamic disinfection methods for a vehicle drinking water tank according to exemplary embodiments of the invention.

FIG. 3 shows a flow diagram which illustrates a method for disinfecting a vehicle drinking water tank according to an exemplary aspect of the invention. The first step S1 represents the provision of a vehicle drinking water tank comprising a spray diffuser inside the vehicle drinking water tank. Furthermore, the partial filling of the vehicle drinking water tank with a disinfecting liquid is represented by the step S2. The third step S3 represents the continuous spraying of the disinfecting liquid, wherein said liquid is sprayed in such a way that a moved film of disinfecting liquid forms over the inner surface of the drinking water tank, whereby the inner surface of the liquid drinking water tank is wetted and disinfected. The partial filling of the drinking water tank (step S2) can thus already be initiated by the spraying process by means of the spray diffuser. Another feed of disinfecting liquid for partial filling is also possible, however.

On the whole, a dynamic disinfection method is thus provided, with which an improved disinfecting effect on the whole can be achieved due to the combination of the chemical and biochemical action of the disinfecting liquid and the shear forces produced by the hydrodynamic flow.

Figure 4:
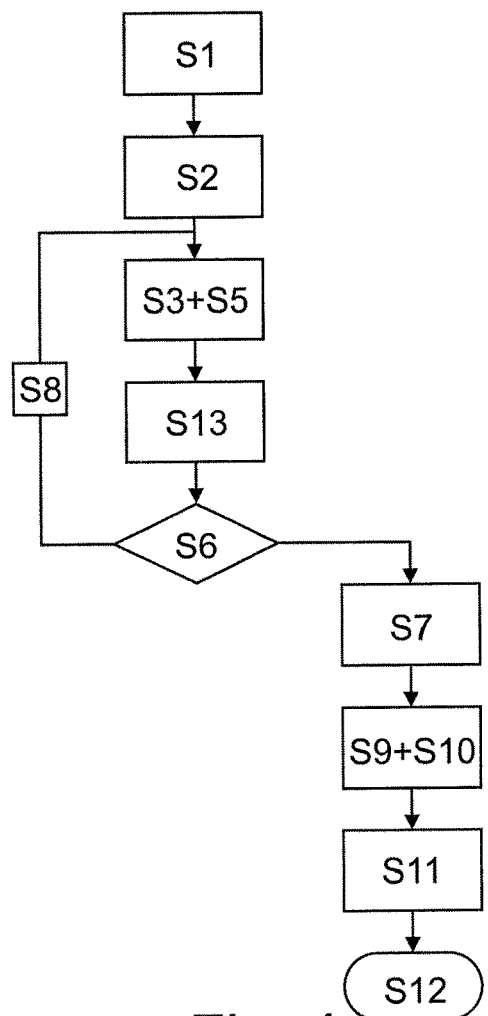

FIG. 4 shows a further flow diagram of a method for disinfecting a vehicle drinking water tank according to a further exemplary aspect of the invention. Steps S1 and S2 are first shown, similarly to the previously described method of FIG. 3. By connecting a pump device, which is represented by the step S5, the disinfecting liquid is pumped through the closed circuit. At the same time, the disinfecting liquid is sprayed (S3) inside the vehicle drinking water tank so that a moved film wets the inner surface of the drinking water tank dynamically, that is to say in a moved manner.

Step S13 describes the pumping of the disinfecting liquid in a separate line branch which is provided for the delivery of drinking water to a consumer. In step S6 it is checked whether the minimal reaction time has already been reached. If this question is answered in the affirmative, step S7 (disconnection of the pump device) follows. If the minimal reaction time has not yet been reached however, step S8 (continuance of pump operation) follows. After step S7, step S9 follows with the opening of an outlet system, whereby the vehicle drinking water tank is relieved of disinfecting liquid. The outlet system is closed in step S10. The drinking water tank is then filled with clean drinking water, which is represented by step S11. Step S12 represents the end of the disinfection method.

Figure 5:
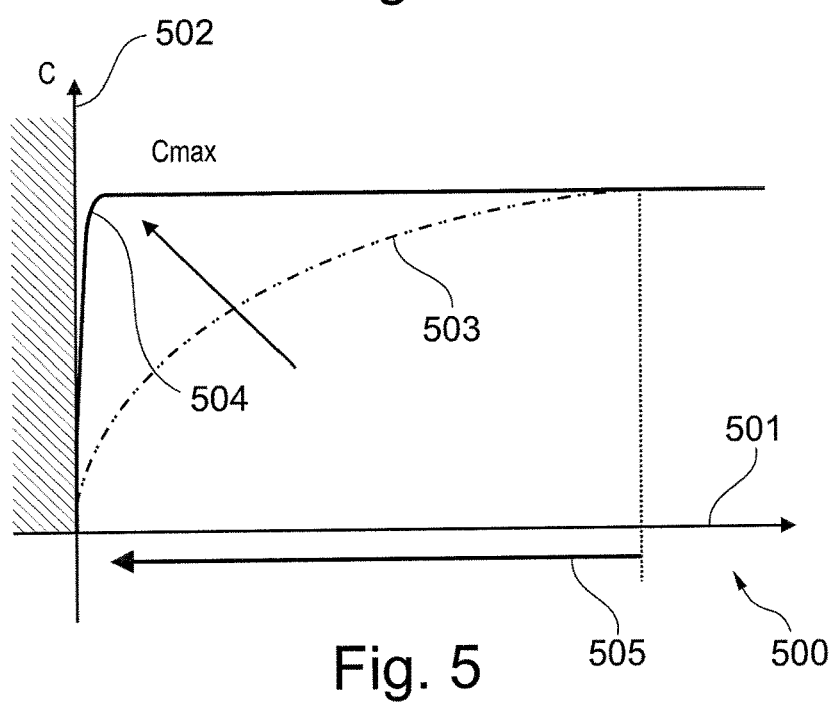
FIG. 5 shows a schematic, two-dimensional illustration of a diagram with regard to the concentration of a disinfecting active ingredient as a function of the state of hydraulic flow and distance from the tank wall.

FIG. 5 shows a graph in which the concentration C of the disinfecting active ingredient is plotted on the vertical axis as a function of the distance from the wall of the tank. The horizontal axis is denoted by 501 and the vertical axis is denoted by 502. Two different curves 503 and 504 are plotted in the graph 500. The concentration of the disinfecting active ingredient may change over time (for example it may reduce). The graph 500 shows the concentration profile at a predefined moment in time. Due to the consumption of disinfecting active ingredient at the wall as a result of the reaction with the biofilm material, the concentration in the vicinity of the wall is lower than that further away from the wall. This can be deduced from both curves 503 and 504. This disadvantageous effect is all the more pronounced in the case of a static situation or if there is only a laminar flow of liquid in the container to be disinfected. This is illustrated by the curve 503, which therefore corresponds to the prior art. In the case of the prior art (graph 503), the material transport is only determined by diffusion processes and the reaction rate in terms of disinfection is limited by the rate of transport of the disinfecting active ingredient towards the inner wall of the transport container and into the biofilm.

By contrast, the curve 504 illustrates a concentration profile which can be achieved if the vehicle drinking water tank according to embodiment of the invention or the dynamic method according to an aspect of the invention is used. In other words: the curve 504 can be achieved if the vehicle drinking water tank according to an embodiment of the invention or the dynamic method according to an aspect of the invention is used. The curve 504 shows an improved profile with increased local concentration of the disinfecting active ingredient in the vicinity of the wall and thus in the biofilm. In other words, the boundary layer 505 is reduced by means of the present invention. This boundary layer denotes the distance which is necessary to achieve a value as close as possible to the saturation value $C_{max}$. In other words, this boundary layer disappears as completely as possible with use of the present invention. This improvement is achieved in practice by producing turbulent flows inside the vehicle drinking water tank and inside the connected line system during the disinfection period. A non-laminar flow is produced, which also increases the mechanical forces on the biofilm. Due to continuous circulation of the disinfecting liquid through the tank and the line system, improved disinfection at higher concentration in the vicinity of the wall is achieved.

In addition, it should be noted that "comprising" does not exclude any other elements or steps and that "a" or "an" does not exclude a plurality. Furthermore, it is noted that features or steps which have been described with reference to one of the above embodiments can also be used in combination with other features or steps of other embodiments described above. Reference numerals in the claims are not to be considered to be limiting.

The invention claimed is:

1. A dynamic disinfection method for a vehicle drinking water tank, said method comprising:
   providing a vehicle drinking water tank with a spray diffuser arranged centrally on a ceiling of the vehicle drinking water tank inside the vehicle drinking water tank;
   partially filling the vehicle drinking water tank with a disinfecting liquid;
   spraying the disinfecting liquid in such a way that a moved film of the disinfecting liquid is formed which wets an inner surface of the vehicle drinking water tank;
   providing a closed circuit between the vehicle drinking water tank and an outer line system;
   connecting a pump device, whereby the disinfecting liquid is pumped through the closed circuit such that the moved film is a continuously moved liquid film over the inner surface;
   pumping of the disinfecting liquid in a separate line branch provided for the delivery of drinking water to a consumer;
   opening of an outlet system, whereby the vehicle drinking water tank is relieved of disinfecting liquid;
   closing the outlet system; and
   filling the drinking water tank with clean drinking water.

2. The disinfection method according to claim 1, further comprising:
   connecting a heating device, whereby the temperature of the disinfecting liquid is changed.

3. The disinfection method according to claim 1, further comprising:
   measuring the temperature of the disinfecting liquid in form of a temperature value;
   transmitting the measured temperature value to a control unit; and
   controlling the heating device by the control unit on the basis of the measured temperature value.

4. The disinfection method according to claim 1, further comprising:
   checking a minimal reaction time;
   disconnecting the pump device in the event that the minimal reaction time is reached; and
   continuing pump operation in the event that the minimal reaction time is not reached.

5. The method of claim 1, wherein the spray diffuser comprises a rotary diffuser.

* * * * *